United States Patent [19]

Hornemann et al.

[11] Patent Number: 5,240,858
[45] Date of Patent: Aug. 31, 1993

[54] **RECOMBINANT VECTOR HAVING A *STREPTOMYCES ACHROMOGENES* DNA SEQUENCE USEFUL FOR GENE AMPLIFICATION**

[75] Inventors: Ulfert Hornemann; Guy G. Hoffman, both of Madison, Wis.; Christopher J. Otto, Pepper Pike, Ohio

[73] Assignee: Wisconsin Alumni Research Foundation, Madison, Wis.

[21] Appl. No.: 639,312

[22] Filed: Jan. 8, 1991

Related U.S. Application Data

[63] Continuation-in-part of Ser. No. 200,992, May 31, 1988, abandoned.

[51] Int. Cl.⁵ .................. C12N 15/63; C12N 15/69; C12N 1/21
[52] U.S. Cl. .................. 435/320.1; 435/69.1; 435/71.2; 435/172.3; 435/252.35
[58] Field of Search ............ 435/320.1, 172.3, 252.35, 435/69.1, 71.2

[56] References Cited

FOREIGN PATENT DOCUMENTS

2153363 8/1985 United Kingdom .

OTHER PUBLICATIONS

J. Schottel et al., 146 J. Bacteriol. 360–368 (1981) (M252 variant of *S. lividans* 1326).
R. Freeman et al., 98 J. Gen. Microl. 453–465 (1977) (chloramphenicol-sensitive strains).
J. Altenbuchner et al., 195 Mol. Gen. Genet. 134–138 (1984) (chloramphenicol-sensitive strains).
U. Hornemann et al., J. Cell Biol. 15th Annual Meeting, Abstract 1982 (1986).
U. Hornemann et al., 5th International Symposium On The Genetics Of Industrial Organisms, Abstract S4-P2 p. 29 (1986).
A. Bertinuson et al., 1984 Meeting Of The American Society For Microbiiology, Abstract Submission Form (abstract published at meeting) (admitted prior art).
C. Otto et al., Wind River Conference On Genetic Exchange, p. 36 (1985).
J. Altenbuchner et al., 5 Bio/Technology 1328–1329 (1987).
J. Altenbuchner et al., 201 Mol. Gen. Genet. 192–197 (1985).
A. Birch et al., 131 J. Gen. Microb. 1299–1303 (1985).
U. Hornemann et al., 169 J. Bacteriol. 2360–2366 (1987) (not prior art).
E. Katz et al., 129 J. Gen. Microb. 2703–2714 (1983).
D. Hopwood et al., 129 J. Gen. Microb. 2257–2269 (1983).
M. Bibb et al., 41 Gene E357–E368 (1986).
C. Thompson et al., 20 Gene 51–62 (1982).
Y. Potekhin et al., 19 Molecular Biology (Russian) 805–817 (1985).
K. Koller et al., 6th International Sym. Biol. Actin, Abstract L71 (1985).
B. Peterson et al., 161 J. Bacteriol. 1042–1048 (1985).
B. Bhuyan et al., Rubradirin, A New Antibiotic, Antimicrob. Agents Chemother. 91–96 (1964).
H. Motamedi et al., 84 P.N.A.S. U.S.A. 4445–4449 (1987).
M. Mori et al., 134 J. Gen. Microb. 85–95 (1988) (not prior art).

*Primary Examiner*—Richard A. Schwartz
*Assistant Examiner*—Nancy Vogel
*Attorney, Agent, or Firm*—Quarles & Brady

[57] ABSTRACT

An improved means for amplifying DNA sequences is disclosed. The invention provides a means for creating tandemly repeated gene sequences. One attaches a selected foreign gene sequence in a *S. achromogenes* fragment and then exposes the recombinant segment to antibiotic challenge. Temperature sensitive plasmids or other curable vectors can be used to assist in the amplification and the positioning of the resulting gene directly in chromosomal host DNA.

3 Claims, 1 Drawing Sheet

5,240,858

RECOMBINANT VECTOR HAVING A *STREPTOMYCES ACHROMOGENES* DNA SEQUENCE USEFUL FOR GENE AMPLIFICATION

This application is a continuation-in-part of application U.S. Ser. No. 07/200,992, filed May 31, 1988, now abandoned.

FIELD OF THE INVENTION

The present invention relates to enzyme and other protein production using genetic engineering techniques. More particularly it relates to the use of part of the gene sequence from the bacterium *Streptomyces achromogenes* to create multiple tandem copies of foreign genes to be expressed.

BACKGROUND OF THE INVENTION

For some time, the art has known that one can clone a foreign gene of interest, and then express it in a suitable host to produce a desired proteinaceous material. Typically, this has been done by inserting a foreign gene (or cDNA version thereof) into a vector (e.g., a plasmid, a virus), and then transforming the host (e.g., a bacteria) with the vector. Commercial production processes for proteins of interest have been built around these concepts.

To improve efficiency and reduce costs, the art has looked for ways to have multiple copies of the foreign gene of interest in a single cell ("amplification"). One commonly employed amplification procedure involves insertion of the foreign gene into a "high copy number" type plasmid, with the subsequent introduction of the plasmid into a suitable host. The host then reproduces a high number of copies of the plasmid inside the cell, thereby creating multiple copies of the gene to be expressed.

However, plasmid instability (and thus a low yield) may result if the inserted genes adversely influence plasmid replication or maintenance.

Thus, the art sought to develop a biological system that automatically produces tandem repetitions of a foreign DNA sequence in the chromosome of a host. In J. Altenbuchner, et al., 201 Mol. Gen. Genet. 192–197 (1985) (the disclosure of this article and all other articles recited herein are incorporated by reference as if fully set forth herein) part of a *Streptomyces lividans* gene sequence which underwent internal amplification was identified. A foreign gene was then inserted in the sequence and amplification of the foreign gene resulted. However, this system probably resulted in mixtures of amplified strains, and is complex.

Thus, a need has existed for an improved means of amplifying foreign genes to be used in protein production independent of the continued presence of a plasmid.

SUMMARY OF THE INVENTION

One aspect of the invention provides a method for creating a desired gene sequence containing a repeated gene sequence. One attaches a copy of a selected foreign gene sequence with a *S. achromogenes* gene sequence. One then exposes the recombinant sequence thus formed to spectinomycin. This method creates a gene sequence containing repeats of at least the portion of the recombinant sequence containing the selected foreign gene. The selected gene sequence is preferably inserted between *S. achromogenes* direct terminal repeats and adjacent to (or in any event associated with) a spectinomycin resistance determinant. In a preferred form, the selected foreign gene sequence is tandemly repeated fifty or more times together with the *S. achromogenes* gene sequence.

In an especially preferred form, the recombinant sequence is positioned in a curable vector (e.g. a temperature sensitive plasmid) which is then exposed to spectinomycin. Curability is the property of a vector which causes it to fail to replicate at high temperature (39° C. versus 28° C.) or other curing conditions. This process can take place while the plasmid is in the bacterium *S. lividans*, with the result that the repeated sequence ends up integrated in the *S. lividans* chromosome. The recombinant *S. lividans* having a properly engineered foreign gene can then directly be used for protein production.

In another form, there is provided a recombinant vector. The vector has a vector backbone (e.g. a curable plasmid), a foreign gene and a *S. achromogenes* gene. The foreign gene is preferably inserted between *S. achromogenes* direct terminal repeats and adjacent to a spectinomycin resistance determinant.

As an alternative, the invention can also provide a different recombinant vector. This vector is a curable plasmid in which a *S. achromogenes* fragment has been inserted. The fragment contains a spectinomycin resistance determinant.

In still another form, the invention provides a recombinant host having in its chromosomal DNA a recombinant *S. achromogenes* gene sequence containing a spectinomycin resistance determinant. The chromosomal DNA also has a repeated gene sequence foreign to both *S. achromogenes* and the host.

It will be appreciated from the discussion above and the disclosure below that a gene sequence of *S. achromogenes* that amplifies itself under antibiotic challenge (to provide antibiotic resistance) has been modified to also permit amplification of a foreign gene of interest. To assist in the amplification in other desired bacterial hosts, e.g. Streptomyces such as *S. lividans* (and perhaps *S. coelicolor*), a curable recombinant vector is used. A tandemly repeated sequence is directly formed in the host chromosomal DNA.

Using this method to create amplified sequences will often be preferable to methods using high copy number plasmids. One reason is that multiple chromosome copies of the cloned foreign gene are being created which may be more stably maintained than the plasmid-borne gene. Also, initial test results indicate that extremely high repetition numbers (e.g. 200–300 repetitions) may result. Also, because this amplification involves an antibiotic resistance gene, the system is easy to work with (e.g. the sequence contains its own marker and is easily selectable).

The objects of the invention therefore include providing processes, vectors, and hosts of the above kind.

DRAWING

FIG. 1 shows a restriction map of a portion of *S. achromogenes;*

DESCRIPTION OF THE PREFERRED EMBODIMENTS

Figure 1:
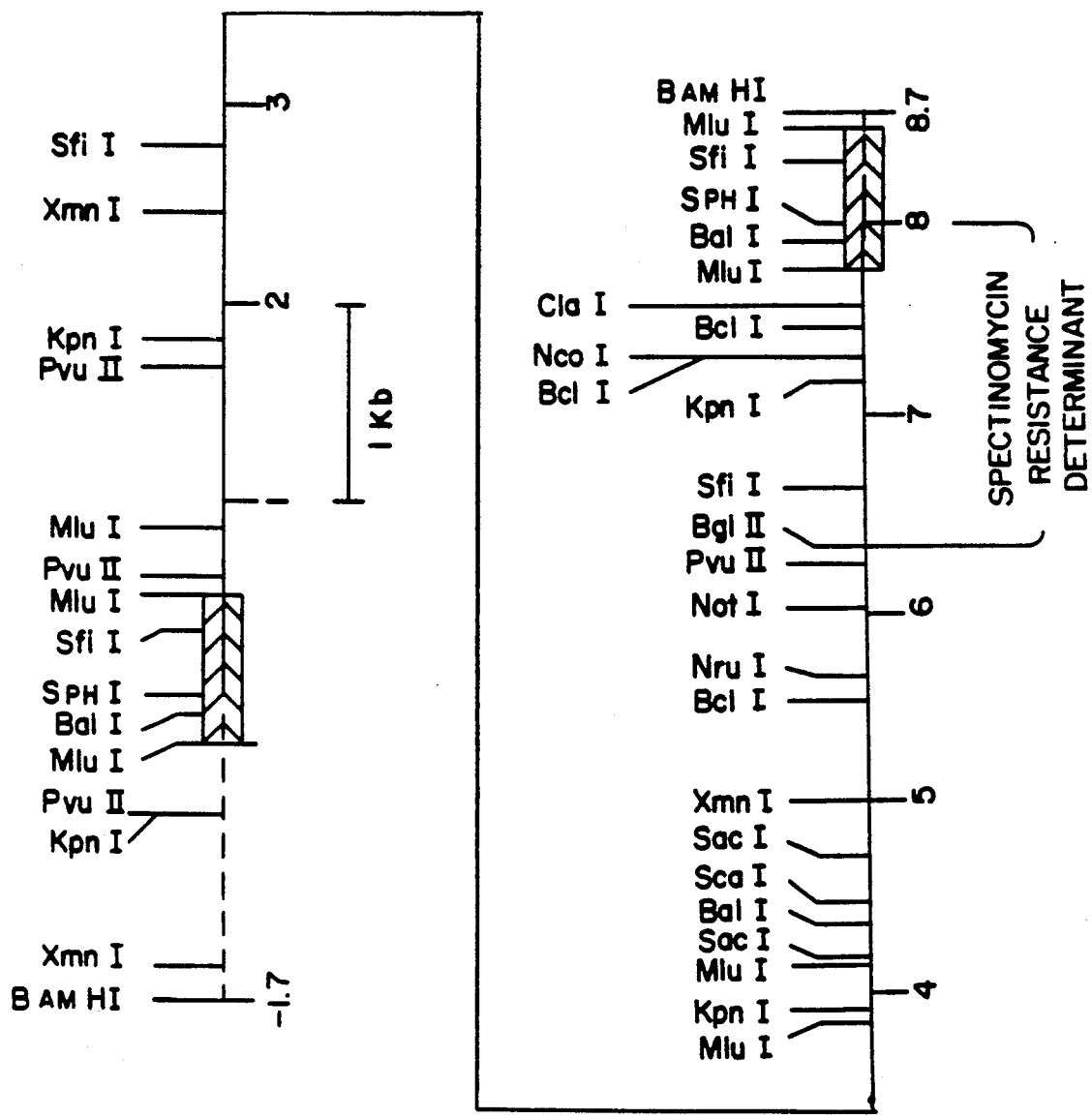

The description below is intended as illustrative of a preferred form of the invention. Thus, the claims are not to be limited to just the preferred embodiment.

Our isolation of a *S. achromogenes* spectinomycin resistance fragment of interest is described in U. Hornemann, et al., 169 J. Bact. 2360-2366 (1987). Briefly, a strain of *Streptomyces achromogenes*, subsp. rubradiris was challenged with antibiotic by plating at low density on 1,000 µg of spectinomycin per ml. This initially produced slow-growing, bald colonies from which arise, in a spatially and temporally random fashion, foci of rapidly growing aerial mycelium-forming cells whose DNA contains an approximately 200- to 300-fold amplification of a particular 8-kilobase (kb) sequence. This sequence was then cloned in *E. coli* on pBR322 and physically characterized. It was separately also cloned in *Streptomyces lividans* as a BglII fragment and shown to impart high-level resistance to spectinomycin.

A spectinomycin resistance determinant was then shown to reside on a 1.7-kb SphI-BglII subfragment. (See FIG. 1) Analysis of Southern blots of restriction enzyme digests of wild-type *S. achromogenes* DNA probed with the labeled 8-kb DNA sequence resulted in the identification and subsequent cloning in *S. lividans* of a 10.4-kb BamHI fragment which includes the complete 8.8-kb amplifiable unit of DNA. This unit carries two 0.8-kb direct repeats as its termini (see FIG. 1) as well as the spectinomycin resistance determinant close to one of these termini.

In preparation of a test of this sequence's ability to amplify, it was ligated as a 10.4-kb BamHI fragment into BglII-cleaved pMT660 (Birch and Cullum, 131 J. Gen. Microbiol. 1299 (1985)). This plasmid is a temperature sensitive replication mutant of pIJ702 (Katz, et al., 129 J. Gen. Microbiol. 2703 (1983)). The resulting plasmid, pBV730ts, was deposited with A.T.C.C. Rockville, Md., on May 27, 1988 as #40455. Samples will be made available as required by applicable law. Such availability is not to be construed as a license to practice the invention.

Protoplasts of the general cloning host *S. lividans* (D. Hopwood, et al., 129 J. Gen. Microbiol. 2257 (1983)) were then transformed with the resulting plasmid pBV730ts. Standard conditions for genetic engineering with *S. lividans* are described in D. Hopwood et al. Genetic Manipulation Of Streptomyces, A Laboratory Manual, John Ihnes Foundation (1985).

At the normal growth temperature of 28° C., pBV730ts is present in *S. lividans* in high copy number and permits efficient expression of spectinomycin resistance without DNA amplification on a variety of growth media. Surprisingly, incubation of *S. lividans* spores containing pBV730ts at the plasmid curing temperature of 39° C. on Hickey Tresner (HT) agar containing 50 µg/ml of spectinomycin (added to the medium to select for progeny that might experience transpositions of key segments during the course of the incubation), yielded some spores that gave rise to mycelia whose DNA contains 200 to 300 copies of an 8-kb tandemly reiterated sequence. The restriction pattern shown by this reiterated DNA was indistinguishable from that of the 8-kb *S. achromogenes* amplified sequence.

None of the *S. lividans* progeny harboring only the 8-kb reiterated DNA were able to grow on media containing the antibiotic thiostrepton for which the vector portion of pBV730ts carries a resistance gene, indicating separation of the vector and the key segment portions of this plasmid. Separate experiments showed the efficient curing of pBV730ts at 39° C. Therefore, the observed amplified DNA appeared to reside in the *S. lividans* chromosome.

It is believed that during growth of *S. lividans* harboring the plasmid pVB730ts on a medium containing 50 µg/ml of spectinomycin at 28°, the spectinomycin resistance determinant functions so as to produce resistance without resorting to amplification. On the other hand, at the elevated temperature (39° C.), the spectinomycin resistance determinant of pBV730ts is expressed inefficiently, necessitating amplification to assure survival. Thus, it appears that other vectors that become unstable at elevated temperatures or in the face of other artificial external challenges may also assist the *S. achromogenes* determinant sequence to amplify.

A highly preferred *S. lividans* strain to observe the transferable DNA amplification is a chloramphenicol-sensitive derivative of the wild-type strain. Such strains (such as the M252 derivative of *S. lividans* 1326, a/k/a *A. ceoelicolor* 66, a/k/a *S. lividans* 66) can easily be isolated by known techniques since they are spontaneously formed at a frequency of about 0.1 to 1% from chloramphenicol-resistant strains. See e.g., D. Hopwood et al., 129 J. Gen. Microb. 2257-2269 (1983); J. Schottel et al., 146 J. Bacteriol. 360-368 (1981); J. Altenbuchner et al., 195 Mol. Gen. Genet. 134-138 (1984); and R. Freeman et al., 98 J. Gen. Microb. 453-465 (1977). Note that the preferred *S. lividans* 66 source was in the John Innes Institute Streptomyces strain collection.

We next explored the possible amplification of "foreign" genes (genes from other sources than *S. achromogenes*). A 1.7 kb DNA fragment, ermE, of *S. erythreus* which imparts resistance to the antibiotic erythromycin Bibb et al., 41 Gene E357 (1986) was inserted into a unique BglII site located in close proximity to the spectinomycin resistance determinant of pBV730ts (see FIG. 1) to generate pBV733ts, which was transformed into *S. lividans* protoplasts at standard conditions. Spores of the resulting transformants were subjected to plasmid curing conditions (selected with spectinomycin and erythromycin) and appropriate work-up. The recovered DNA samples revealed a 9.7 kb amplified DNA sequence representing approximately 200 to 300 copies of chromosomally integrated pBV733ts-derived sequences. The 9.7 kb amplified DNA is composed of the *S. achromogenes* 8.0 kb Sph I fragment (see FIG. 1) and the 1.7 kb ermE insert.

It is concluded from this experiment that insertion of the ermE gene into the BglII site of pBV730ts creates a mutant that yields amplification of pBV733ts sized DNA sequences.

As a second experiment, a 1.2-kb DNA fragment, aph, of *S. fradia* encoding the enzyme aminoglycoside phosphotransferase, which imparts resistance to the antibiotic neomycin (Thompson, et al., 20 Gene 51 (1982)) was inserted into the unique Sca I site located in the *S. achromogenes* portion of pBV730ts to generate pBV738ts, which was transformed into *S. lividans* protoplasts. Spores of the resulting transformants were subjected to plasmid curing conditions by incubating them at 39° C. on HT agar in the presence of 50 µg/ml of spectinomycin. The resulting mycelia were streaked out on antibiotic-free HT agar to obtain single colonies which were then patched to antibiotic-free HT agar and to HT agar containing 100 µg/ml of spectinomycin, 50 µg/ml of thiostrepton and 10 µg/ml of neomycin, respectively. Using these techniques, a 9.2 kb amplified sequence composed of the *S. achromogenes* 8.0 kb Sph I fragment (see FIG. 1) and the 1.2 kb insert can be obtained.

We claim:

1. A recombinant vector comprising a vector backbone, a gene foreign to *S. achromogenes*, and a *S. achromogenes* gene sequence having direct terminal repeats, the *S. achromogenes* direct terminal repeats being associated with a spectinomycin resistance determinant, the foreign gene sequence being inserted between the *S. achromogenes* direct terminal repeats, and the determinant and direct terminal repeats having a nucleotide sequence that is also present in a *S. achromogenes* portion of pBV730ts.

2. The recombinant vector of claim 1, wherein the vector backbone is curable.

3. The recombinant vector of claim 2, wherein the vector backbone is temperature curable.

* * * * *

UNITED STATES PATENT AND TRADEMARK OFFICE
CERTIFICATE OF CORRECTION

PATENT NO. : 5,240,858
DATED : August 31, 1993
INVENTOR(S) : Ulfert Hornemann, et al.

It is certified that error appears in the above-identified patent and that said Letters Patent is hereby corrected as shown below:

On title page, item [56]
OTHER PUBLICATIONS:
    Society For Microbiiology        s/b Society For Microbiology Column 1, Line 63:
    sequence with a        s/b sequence within a Column 2, Line 31:
    recombi7        s/b recombi Column 2, Line 53:
"anti7"        s/b anti Column 2, Line 62:
    achromogenes;        s/b achromogenes.

Column 4, Line 53:
    fradia        s/b fradiae

Signed and Sealed this

Twelfth Day of April, 1994

*Attest:*

BRUCE LEHMAN

*Attesting Officer*    *Commissioner of Patents and Trademarks*